United States Patent [19]
Schuger et al.

[11] Patent Number: 5,140,987
[45] Date of Patent: Aug. 25, 1992

[54] METHOD FOR TRANSVENOUS ABLATION OF CARDIAC ELECTRICALLY CONDUCTIVE TISSUE BY LASER PHOTOCOAGULATION

[75] Inventors: Claudio Schuger, Ann Arbor; Russell T. Steinman, Southfield, both of Mich.

[73] Assignee: Wayne State University, Detroit, Mich.

[21] Appl. No.: 774,383

[22] Filed: Jan. 19, 1991

Related U.S. Application Data

[63] Continuation of Ser. No. 574,499, Aug. 27, 1990, abandoned, which is a continuation of Ser. No. 324,768, Mar. 17, 1989, Pat. No.

[51] Int. Cl.⁵ .......................... A61B 5/04; A61N 5/00
[52] U.S. Cl. ...................................... 128/642; 606/15
[58] Field of Search ............ 128/642, 398, 786, 419 P; 606/15, 16

[56] References Cited

U.S. PATENT DOCUMENTS 4,777,955 10/1988 Brayton et al. ..................... 128/642
4,785,815 11/1988 Cohen ................................ 128/642
4,799,479 1/1989 Spears ............................. 128/303.1
4,860,743 8/1989 Abelan ............................. 606/16

FOREIGN PATENT DOCUMENTS 0249631 9/1987 Fed. Rep. of Germany ...... 128/786

OTHER PUBLICATIONS

*USCI Catalog*, p. 5, Jun. 1974.

*Primary Examiner*—Lee S. Cohen
*Attorney, Agent, or Firm*—Reising, Ethington, Barnard, Perry & Milton

[57] ABSTRACT

The invention provides an apparatus and method for the ablation of cardiac electrically conductive tissue by laser photocoagulation. Reference points of cardiac tissue to be ablated are transvenously mapped. A laser balloon catheter having electrodes positioned on each lateral aspect of the balloon is transvenously positioned in the coronary sinus a the predetermined reference points. The electrodes are used to localize the laser balloon by detecting electrical activity of the tissue adjacent to the laser balloon at the area to be ablated. The tissue area adjacent the balloon is then irradiated to thermally damage the cardiac tissue outside of the vein and adjacent the balloon to render the cardiac tissue electrically inert.

4 Claims, 1 Drawing Sheet

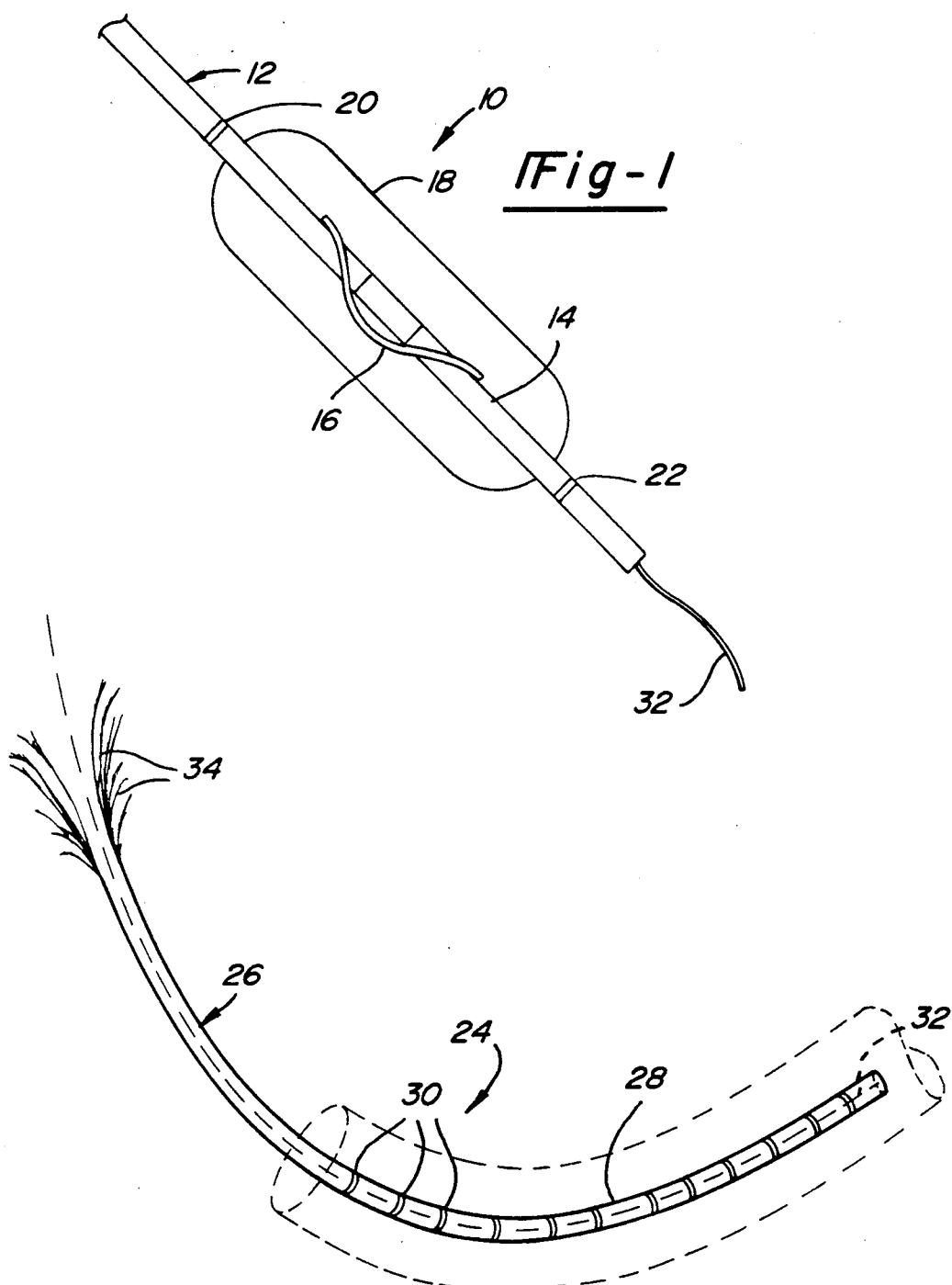

METHOD FOR TRANSVENOUS ABLATION OF CARDIAC ELECTRICALLY CONDUCTIVE TISSUE BY LASER PHOTOCOAGULATION

This application is a continuation of application Ser. No. 574,499, filed Aug. 27, 1990 now abandoned; which is a continuation of Ser. No. 324,768 filed Mar. 17, 1989 now abandoned.

TECHNICAL FIELD

The present invention relates to a method of percutaneous ablation of conductive pathways of tissue, such as cardiac tissue. More specifically, the present invention can be utilized for the percutaneous ablation of left sided accessory pathways in patients with symptomatic arrhythmias by means of thermocoagulation with a Nd:YAG laser balloon catheter positioned in the coronary sinus.

BACKGROUND OF THE INVENTION

Catheter ablation of posteroseptal accessory pathways through the coronary sinus by means of direct current electrical shock is an accepted technique for the treatment of drugresistant patients of the Wolff-Parkinson-White syndrome. Morady F., Scheinman MM, Winston SA, et al; efficacy and Safety of Transcatheter Ablation of Posteroseptal Accessory Pathways—Circulation 72:170, 1985. The Wolff-Parkinson-White syndrome is frequently associated with rapid supraventricular arrhythmias that are related to the presence of accessory atrioventricular connections, which are usually in close contiguity to the coronary sinus. These rhythm disturbances are usually symptomatic and may be life threatening in a subset of patients. Klein GJ, Bashore TM, Sellers TD, et al: Ventricular Fibrillation in the Wolff-Parkinson-White Syndrome. N. Engl. J. Med. 01:1080, 1979. Drug therapy has been effective for suppressing or controlling many of these arrhythmias. With many patients, surgery is becoming the treatment of choice. Prystowsky EN, Pressley JC, Gallagher JJ, et al: The Quality of Life and Arrhythmia Status After Surgery for Wolff-Parkinson-White Syndrome: an 18 years perspective. JACC 9:100A, 1987. The possibility of avoiding surgery by achieving destruction of accessory pathways with ablative techniques represents a major breakthrough in the treatment of the disease. Presently, available ablation techniques involving the coronary sinus are limited to accessory pathways located in the posteroseptal area. The ability to safely and effectively ablate left free wall accessory atrioventricular connections (the most prevalent variety) using laser energy delivered percutaneously via a catheter would represent a significant advance in the management of this disease.

The term "ablative techniques" refers to the use of physical agents capable of modifying conduction in a restricted area of the myocardium for treating or preventing cardiac arrhythmias without losing the structural integrity of the tissue. Fontaine G, Scheinman MM: Ablation in Cardiac Arrhythmias. Futura Publishing Company, Inc., Mount Kisco, N.Y., 1987. There have been several reports of a therapeutic application of intraoperative ablative techniques to sever the normal atrioventricular conduction system. Gianelli S, Ayers SM, Gomprecht RF, et al: Therapeutic Surgical Division of the Human Conduction System. JAMA 199:155, 1968. Slama R., Blondeau P, Aigueperse J, et al: Creation Chirurgicale d'un Bloc Auriculoventriculaire et implantation d'un Stimulateur daus deux cas de Troubles du Rythme Irreductibles. Arch. Med Geur Vaisseaux 60:406, 1967. Other reports have observed the effect of ablation on other conductive systems. Cobb FR, Blumenschein DF, Sealy WC, et al: Successful Surgical Interruption of the Bundle of Kent in a Patient with Wolff-Parkinson-White Syndrome. Circulation 38:1018, 1968. Vedel J, Frank R, Fontaine G, et al: bloc Avriculoventriculaire Intrahisien Definitif Induit au Cours D'une Exploration Endoventriculaire Droit. Arch Med Coeur Vaisseaux 72:107, 1979. Scheinman MM, Morady F, Hess D, et al: Catheter-induced Ablation of the Atrioventricular Junction to Control Refractory Supraventricular Arrhythmias. JAMA 248:851,1982. Gallagher JJ, Svenson RH, Kasell JU, et al: Catheter Technique for Closed-Chest Ablation of the Atrioventricular Conduction System. A Therapeutic Alternative for the Treatment of Refractory Supraventricular Tachycardia. N Eng J Med 306:194, 1982.

It has been suggested that the anatomic relationship of the close proximity of the atrioventricular accessory pathways through subepicardial fat of the atrioventricular groove in close proximity to the coronary sinus may be used to create localized lesions from the coronary sinus using different energy sources, such as direct current electrical shock or radio frequency in an effort to ablate the anomulous atrioventricular connections. Morady F, Scheinman MM: Transvenous Catheter Ablation of A Posteroseptal Accessory Pathway in a Patient with the Wolff-Parkinson-White Syndrome. N. Eng J Med 310:705, 1984. Morady first described the use of this transvenous technique using high energy direct electrical shock. In patients with posteroseptal accessory pathways, this technique has gained increasing popularity as an appealing alternative to surgery due to its high success rate and low incidence of complications. Morady, F., Scheinman, M.M.: Catheter Ablation of Accessory Pathways, Scheiman, M.M. (Ed.): Catheter Ablation of Cardiac Arrhythmias, Martinez Pub. Nighoff Publishing, Boston, pp.163-164. However, a much lower success rate has been achieved for left free wall accessory pathways where the rate of complications of high energy electrical shocks is very high. Fisher JD, Brodman R, Kim SG, Matos JA, Brodman E, Wallerson D, Waspe LE: Attempted Non-Surgical Electrical Ablation of Accessory Pathways via the Coronary Sinus in the Wolff-Parkinson-White Syndrome. JACC 4:685, 1984. This difference is due to the anatomic variations in susceptibility to barotrauma secondary to high energy electrical current shocks. Attempts to reduce the electrical energy to prevent complications have proved to be ineffective for ablations of left sided pathways. Fisher et al, supra.

Radiofrequency current has been proposed as an alternative energy source for catheter ablations. Huang SK, Graham AR, Bharati S, Lee MA, Gorman G, Lev M: Short and Long Term Effects of Transcatheter Ablation of the Coronary Sinus by Radiofrequency Energy. Circulation 78:416,1988. In this technique, current is delivered at a low power during longer periods of time to achieve tissue desiccations. This technique is relatively free of complications, but appears to have a lower success rate than direct current electrical shocks in the few clinical studies that have been published. Borggrefe M, Budde T, Martinez-Rubio A, Hindricks G, Haverkamp W, Gulker H, Breithardt G: Radiofrequency Catheter Ablation for Drug-Refractory Supraventricular Tachycardia. Circulation 78, II:305, 1988.

Studies have shown that the use of the ND:YAG laser provides the best available laser wavelength to achieve subsurface penetration and thermocoagulation of tissue. McCord RC, Weinberg W, Gorisch W, et al: Thermal Effects of Laser Irradiated Biology Tissue. In: Proceedings, Symposium In Laser in Medicine and Biology. GSF-Berichte, BPT 5, Neuherberg, 1977. Further, unlike other laser delivery systems, the ND:YAG laser balloon catheter distributes energy to a significant area of the coronary sinus thereby resolving the problem of targeting an otherwise narrow laser beam. The ND:YAG laser balloon catheter has been developed for percutaneous transluminal coronary angioplasty restenosis prevention. Spears JR: Percutaneous Transluminal Coronary Angioplasty Restenosis: Potential Prevention WIth Laser Balloon Angioplasty. Am J Cardiol 60:61B, 1987.

The present invention provides means for ablating electrically conductive tissue by laser photocoagulation. It further provides means for pacing and recording thereby allowing the localization of the accessory pathways to be ablated. This features, in combination with a novel mapping method and apparatus, provide an improved means for ablation of cardiac electrically conductive tissue by laser photocoagulation. More specifically, the present invention provides the means for more precise and effective catheter ablation of all left sided accessory pathways thereby providing a treatment for drug resistant patients having the Wolff-Parkinson-White syndrome.

SUMMARY OF THE INVENTION

In accordance with the present invention, there is provided a method of ablating cardiac electrically conductive tissue by laser photocoagulation, the method including the steps of transvenously mapping reference points of cardiac area to be ablated and transvenously positioning a laser balloon catheter at the predetermined reference points. The area adjacent the balloon is irradiated by the laser, thermally damaging the cardiac tissue and rendering the tissue electrophysiologically inert.

FIGURES IN THE DRAWINGS

Other advantages of the present invention will be readily appreciated as the same becomes better understood by reference to the following detailed description when considered in connection with the accompanying drawings wherein:

FIG. 1 is a schematic cross sectional view of a laser balloon catheter constructed in accordance with the present invention; and FIG. 2 is a schematic cross sectional view of a mapping catheter constructed in accordance with the present invention.

DETAILED DESCRIPTION OF THE DRAWINGS

A laser balloon catheter constructed in accordance with the present invention is generally shown at 10 in FIG. 1. The catheter 10 includes a fiberoptic support shaft generally shown at 12 having a distal termination portion 14. The shaft 12 is of the type for conducting laser energy from a source to a diffusing tip 16. The diffusing tip 16 is a helical diffusing tip wound about the distal termination portion 14. An inflatable balloon 18 is mounted on the distal termination 14 over the tip 16. Such a device has been disclosed in detail in several articles cited above. e.g. Spears, supra. The device further includes localizing means mounted on the distal termination 14 for detecting electrically conductive activity of tissue adjacent the balloon 18.

More specifically, the localizing means includes a pair of unipolar electrodes 20,22 mounted on the distal termination 14 adjacent each end of the balloon 18. The electrodes 20,22 are capable of recording electrical activity of conductive tissue adjacent the balloon 18 and thereby adjacent the diffusing tip 16 for detecting electrical activity of the tissue adjacent the catheter. If the catheter is positioned within a cardiac vessel, the electrodes 20,22 can record electrical activity of the adjacent cardiac tissue extension to the vessel.

An example of a laser balloon catheter used with the present invention is an instrument comprising an 8Fr double-lumen balloon catheter with an optical fiber terminating in the cylindrical diffusing tip 16 in the central portion of a two centimeter long, 3 millimeter diameter balloon such as that disclosed in the Spears article, supra. In animal models, an ND:YAG CW laser (1.060 nm) radiation is delivered via the optical fiber in the catheter so as to achieve a total energy of 450 J ($35W \times 5$ sec $25W \times 5$ sec, $15W \times 10$ sec) (during a 20 second exposure). An estimated plateau temperature of approximately 125° C. 0.5 to 1 mm from the balloon surface and approximately 80° C. to 90° C. 3 mm from the balloon surface can be achieved with this dose. Jenkins RD, Sinclair IN, Anand RK, James LM, Spears JR: Laser Balloon Angioplasty: Effect of Exposure Duration on Shear Strength of Welded Layers of Postmortem Human Aorta. Lasers in Surgery and Medicine 8:392, 1988.

The balloon 18, when inflated, displaces blood from the tip 16 within the vessel and the tissue to be irradiated, thereby removing the highly absorbant blood interface between the balloon and the vessel wall. This results in improved efficiency of the thermocoagulation. Secondly, the balloon 18 dilates the vein which is then in essence fixed by the thermocoagulation process. Since the thermocoagulation process reduces the elastic recoil of the tissue, the vein will remain in the expanded condition once the balloon 18 is deflated.

The electrodes 20,22, either unipolar or bipolar, provide for improved localization of the laser balloon which is necessary to insure that the area which is to be ablated is in actuality the area which is ablated. The electrodes 20,22 allow for a mapping of this structure within 1–2 cm thereby insuring that the 1–1.5 cm irradiation extent of the laser 16 irradiates the predetermined area which is to be ablated. As discussed below, this device can be useful for ablation of otherwise hard to discern cardiac pathways, such as the left sided accessory pathways which must be ablated for the effective treatment of Wolff-Parkinson-White Syndrome.

Utilization of the present invention provides a novel method of ablation of cardiac electrically conductive tissue by laser photocoagulation. The method generally includes the steps of transvenously mapping reference points of the cardiac area to be ablated, tranvenously positioning the laser balloon catheter at the predetermined reference points, localizing the laser balloon by detecting electrical activity of the cardiac tissue adjacent the laser balloon at the area to be ablated, and irradiating the cardiac tissue area adjacent the balloon and thermally damaging the cardiac tissue and rendering the cardiac tissue electrophysiologically inert. The irradiated cardiac tissue is made electrically silent while the tissue maintains structural integrity.

The present invention also provides a novel means of initially mapping reference points of cardiac area to be ablated. This mapping procedure can be used as a preablation procedure at the operators discretion. The mapping procedure utilizes a multi-polar electrode catheter specially devised to facilitate accurate electrophysiologic localization or "mapping" of the accessory pathway prior to introduction of the laser balloon.

The mapping catheter is generally indicated at 24 in FIG. 2. The catheter 24 includes a hollow soft support shaft generally shown at 26 having a distal end portion 28. A plurality of ring electrodes 30 are mounted on and spaced at regular intervals over the distal end portion 28. The catheter 26 is hollow so as to be able to slide over an internal guide wire 32. The electrode wires 34 would be connected to a recording device, not shown.

Initially, a soft tipped guide wire 22 is introduced into the coronary sinus by a specially designed guiding catheter. The location of the guiding catheter and guide wire 32 will be confirmed by a fluoroscopy. This allows access of the mapping catheter 24 to lateral positions of the coronary sinus which currently may be difficult to reach with conventional stiff electrode catheters. Unlike the stiff electrode catheters, the mapping catheter includes a soft support shaft 26. Once positioned, the mapping catheter 24 detects electrical activity and records the electrical activity along the atrioventricular groove. By being soft, the mapping catheter 24 can be guided over the guide wire 32. The ability to navigate this flexible catheter 24 laterally along the atrioventricular groove enhances the likelihood that the accessory pathway location can be truly bracketed or electrically mapped between several electrodes during electrophysiologic mapping.

Once the conduction times are documented for the region corresponding to the presumed accessory pathway location, these parameters can be recorded for later reproduction using electrodes 20,22 surrounding the balloon 18 of the laser balloon ablation catheter 10.

Once mapping is completed, the mapping catheter 24 is removed from the guide wire 32. The laser balloon catheter 10 is then entrained over the guide wire 32, as shown in FIG. 1. The laser balloon catheter 10 is positioned accordingly with the previously determined reference points mapped by the mapping catheter 24. Confirmation of the precise location of the helical diffusing tip 16 is achieved by unipolar or bipolar recordings obtained via the electrodes 20,22 of the laser balloon catheter 10. In other words, localization of the heat producing helical diffusing tip is achieved by the electrodes 20,22 reproducing the reference points initially mapped by a conventional electrode catheter or by the mapping electrode 24 and pacing and recording the electrical activity of the adjacent area with the electrodes 20,22 positioned on either longitudinal end of the lasing port of the laser balloon catheter 10 adjacent to the tissue to be ablated.

Upon precise localizing of the helical diffusing tip, the area adjacent the balloon 18 is irradiated to electrically silence the cardiac tissue adjacent the balloon 18 while the tissue maintains structural integrity. This is achieved by the application of the laser energy through the balloon, the laser energy penetrating and thermocoagulating the adjacent tissue so as to render the tissue electrophysiologically inert.

The functional disappearance of the accessory pathway can be confirmed by the reference electrodes of the laser balloon catheter.

Of course, the present invention can be used for other ablations where mapping of the area to be ablated is critical and positioning of the helical diffusing tip is critical. Thusly, the present invention provides a novel apparatus and process for first mapping the area to be ablated and then for localizing the laser irradiating portion of the ablation catheter.

EXPERIMENTS

Three canine studies have been performed utilizing the Spears TM laser balloon angioplasty catheter in coronary sinus. The first study was a feasibility study using 35 watts of Nd:YAG laser energy delivered over 20 seconds (total energy, 700 J) to the distal coronary sinus, resulting in localized coagulation necrosis of the region of the atrioventricular groove. There were no adverse hemodynamic or electrocardiographic sequelae. Coronary angiography revealed no evidence of circumflex coronary artery stricture or thrombosis and no coronary sinus thrombosis or perforation. There was no evidence of mitral regurgitation during post-ablation ventriculography.

Different doses of laser energy also delivered to coronary sinus were used respectively, in two additional dogs: i) 35 W$\times$10 sec followed by 25 W$\times$5 sec followed by 15 W$\times$5 sec (total 550 J), applied three consecutive times (grand total 1650 J); and ii) 35 W "ramped" downward to 15 W over a 20 sec period (total 600 J), again applied three consecutive times (grand total 1800 J). Even at these higher energies there was no evidence of hemodynamic, electrographic or arteriographic damage; moreover, mitral valve competence was maintained. Yet, in both these cases coagulation necrosis extended beyond the atrioventricular groove into the atrial wall— indicating damage to the very region through which accessory pathway fibers are known to course in humans.

The present invention provides an effective means for ablation of cardiac electrically conductive tissue by laser photocoagulation. Evidence of the feasibility of this process at the coronary sinus makes it a prime candidate for the treatment of Wolff-Parkinson-White syndrome. To achieve this, the invention would be specifically used for the ablation of the abnormal conduction pathways associated with Wolff-Parkinson-White syndrome.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. Method of transvenously inactivating cardiac electrically conductive tissue by laser photocoagulation, said method including the steps of: transvenously mapping reference points of a cardiac area to be inactivated; transvenously positioning a laser balloon catheter in a vessel at the mapped reference points, the laser balloon catheter transiently interrupting blood flow in the vessel and disposing the laser balloon adjacent to the vessel; and irradiating laser light from the laser balloon catheter and thereby heating through the catheter a tissue area adjacent the balloon and thermally inactivating the cardiac tissue adjacent the vessel containing the catheter and rendering the irradiated cardiac tissue electrophysiologically inert while maintaining structural integrity of the vessel and cardiac tissue.

2. A method as set forth in claim 1 further including the step of localizing the laser balloon by detecting electrical activity of the tissue adjacent the laser balloon at the area to be inactivated.

3. A method as set forth in claim 2 wherein the laser balloon catheter includes a lasing port, said localizing step being further defined as reproducing the reference points initially mapped to positively position the lasing port of the laser balloon catheter adjacent the cardiac tissue to be inactivated.

4. Method of transvenously inactivating cardiac electrically conductive tissue by laser photocoagulation, said method including the steps of: transvenously mapping reference points of cardiac area to be inactivated by transvenously introducing a soft tipped guide wire allowing access of a catheter to a tissue area to be mapped, entraining a soft hollow mapping catheter having spaced electrodes thereon over the guide wire and to the tissue area to be mapped; and recording conduction times of a tissue area corresponding to the area to be inactivated through the electrodes; transvenously positioning a laser balloon catheter at the mapped reference points by detecting electrical activity of the tissue adjacent the laser balloon at the area to be inactivated, recording the electrical activity of the tissue to be inactivated with two unipolar or bipolar electrodes, one of said electrodes being mounted at each end of the balloon of the balloon catheter, reproducing the reference points initially mapped by said recording with the electrodes to positively position a lasing port of the laser balloon catheter adjacent the tissue to be inactivated; and irradiating light from the laser port of the laser balloon catheter for generating heat from said laser balloon catheter to the tissue area adjacent the laser balloon catheter for thermally damaging the cardiac tissue adjacent the balloon and rendering the irradiated cardiac tissue electrophysiologically inert.

* * * * *